(12) United States Patent
Rowe et al.

(10) Patent No.: US 9,452,318 B2
(45) Date of Patent: Sep. 27, 2016

(54) EXERCISE APPARATUS AND RELATED METHODS AND COMPUTER PROGRAM PRODUCTS

(71) Applicant: East Carolina University, Greenville, NC (US)

(72) Inventors: David Anthony Rowe, Glasgow (GB); Matthew Thomas Mahar, Greenville, NC (US)

(73) Assignee: East Carolina University, Greenville, NC (US)

( * ) Notice: Subject to any disclaimer, the term of this patent is extended or adjusted under 35 U.S.C. 154(b) by 524 days.

(21) Appl. No.: 13/833,062

(22) Filed: Mar. 15, 2013

(65) Prior Publication Data

US 2013/0282156 A1 Oct. 24, 2013

Related U.S. Application Data

(60) Provisional application No. 61/637,425, filed on Apr. 24, 2012.

(51) Int. Cl.
*A63B 24/00* (2006.01)
*A61B 5/103* (2006.01)
*G06F 19/00* (2011.01)

(52) U.S. Cl.
CPC .......... *A63B 24/0003* (2013.01); *A61B 5/103* (2013.01); *G06F 19/3481* (2013.01)

(58) Field of Classification Search
USPC .................................. 700/91; 463/20, 25, 30
See application file for complete search history.

(56) References Cited

U.S. PATENT DOCUMENTS

| | | | |
|---|---|---|---|
| 4,525,074 A | 6/1985 | Murakami | |
| 6,229,764 B1 | 5/2001 | Tongue | |
| 6,571,193 B1 * | 5/2003 | Unuma et al. | 702/141 |
| 6,669,600 B2 | 12/2003 | Warner | |
| 6,700,499 B2 | 3/2004 | Kubo et al. | |
| 6,796,925 B2 | 9/2004 | Martinez et al. | |
| 7,877,226 B2 | 1/2011 | Chan et al. | |
| 7,901,324 B2 | 3/2011 | Kodama | |
| 7,909,741 B2 | 3/2011 | Kim et al. | |
| 7,967,728 B2 * | 6/2011 | Zavadsky et al. | 482/5 |
| 2010/0080087 A1 * | 4/2010 | Shupp | 368/14 |
| 2010/0113225 A1 | 5/2010 | Mills et al. | |
| 2013/0123955 A1 * | 5/2013 | Greenberg et al. | 700/91 |

* cited by examiner

*Primary Examiner* — Paul A D'Agostino
*Assistant Examiner* — Brandon Gray
(74) *Attorney, Agent, or Firm* — Myers Bigel & Sibley, P.A.

(57) ABSTRACT

A portable exercise apparatus for use by a user performing push-ups includes: a detection device; and a suspension member adapted to suspend the detection device from the user. When the detection device is suspended from the user by the suspension member, the apparatus is operative to indicate execution of a compliant push-up by the user.

14 Claims, 7 Drawing Sheets

EXERCISE APPARATUS AND RELATED METHODS AND COMPUTER PROGRAM PRODUCTS

RELATED APPLICATIONS

This application claims priority from U.S. Provisional Application No. 61/637,425, filed Apr. 24, 2012, the disclosure of which is hereby incorporated herein in its entirety.

BACKGROUND

The push-up is a widely used measure of upper body strength. For example, push-ups are used in connection with the FitnessGram® youth fitness test, the President's Challenge Physical Fitness Test and the Army Physical Fitness Test (APFT). These programs all define a correctly performed push-up in a similar way: FitnessGram® uses the term 90 degree push-up; the President's Challenge calls them right angle push-ups; and the APFT defines them as "lowering your entire body as a single unit until your upper arms are at least parallel to the ground."

During push-ups, the most common difficulty for people doing the push-ups and for people judging/counting the push-ups is to determine whether the performer is in the correct "down" position (i.e., elbows at 90 degrees). In many settings, especially where mass testing is needed (e.g., schools and the military), judging/counting of push-ups is often done by other people being tested (e.g., other students or other military personnel). This leads to inconsistency because on different occasions a person may be judged/tested by different people. This also leads to inaccurate scoring because the people doing the judging do not have the expertise to accurately determine whether the person being tested is in the correct "down" position. Further, a person self-judging/self-testing often does not know whether he/she is performing the push-ups correctly.

Various devices have been proposed to assist in determining whether a user is correctly performing push-ups. However, each of these devices suffers from drawbacks including: bulkiness, complexity, high cost, inaccuracy, inability to be adjusted for users of various sizes, and lack of feedback to the user and/or observer.

Thus, there is a need for a device that is simple to understand and use, relatively inexpensive, small enough to be easily transported, can be used in a variety of settings such as at the gym or at home, provides feedback to the user and/or observer, and is adjustable such that it accurately determines whether push-ups are being correctly performed regardless of the size of the user. These and other advantages of the invention will be apparent in the description that follows.

SUMMARY

According to a first aspect, embodiments of the invention are directed to a portable exercise apparatus for use by a user performing push-ups. The apparatus includes a detection device and a suspension member adapted to suspend the detection device from the user. When the detection device is suspended from the user by the suspension member, the apparatus is operative to indicate execution of a compliant push-up by the user.

In some embodiments, the suspension member has a length, and the apparatus includes an adjustment member connected to the suspension member, with the adjustment member configured to adjust the length of the suspension member. The length of the attachment member may be adjustable to a user's forearm length by receiving the detection device in the user's palm with the user's elbow at a substantially right angle, looping the attachment member beneath the user's elbow and moving the adjustment member upward until it resides against or proximate the user's elbow. In some embodiments, wherein the user performs push-ups between an up position and a down position, and wherein, when the length of the attachment member is adjusted to the user's forearm length: in the up position, the user's upper arm is substantially perpendicular to the ground and the detection device is suspended above the ground; and in the down position, the user's upper arm is substantially parallel to the ground and the detection device contacts the ground. The detection device provides audible, tactile, visual and/or proprioceptive feedback.

The suspension member may be connected to and extend away from the detection device in a looped configuration, with the suspension member configured to suspend from the user's neck.

In some embodiments, the apparatus includes an actuator disposed on the detection device, wherein the user performs push-ups between an up position and a down position, and wherein: in the up position, the user's upper arm is substantially perpendicular to the ground and the detection device is suspended above the ground; and in the down position, the user's upper arm is substantially parallel to the ground and the detection device contacts the ground such that the actuator is actuated. The apparatus may include a counter disposed on the detection device, with the counter configured to incrementally display a number of times the actuator is actuated.

According to a second aspect, embodiments of the invention are directed to a portable exercise apparatus for use by a user performing push-ups. The apparatus includes a detection device attached to or carried by the user. The detection device includes: a housing; an accelerometer held in the housing; and a controller held in the housing. The controller is configured to: receive data from the accelerometer; determine when a compliant push-up has been performed based on the received data, wherein a compliant push-up is a push-up meeting prescribed criteria; and monitor the number of compliant push-ups that have been performed.

In some embodiments, the accelerometer is configured to trace a path of movement of the user, and the controller is configured to determine when a compliant push-up has been performed when the user has moved a threshold distance along the traced path of movement and/or a when the user has moved past a threshold position along the traced path of movement. The threshold distance and/or the threshold position may be based on the prescribed criteria. The controller may be configured to use an algorithm to process the data received from the accelerometer, analyze the data, and re-establish the criteria for a compliant push-up.

The detection device may include at least one of: a display configured to display the number of compliant push-ups that have been performed; and an audio output device configured to provide audible feedback when the user has performed a compliant push-up.

According to a third aspect, embodiments of the invention are directed to a system for monitoring push-ups. The system includes at least one detection device, each one attached to or carried by a respective user. Each detection device includes: a housing; an accelerometer held in the housing; and a transmitter configured to wirelessly transmit data from the accelerometer. The system includes a remote device including: a receiver configured to wirelessly receive data transmitted from the at least one detection device; and a controller. The controller is configured to: determine when a compliant push-up has been performed based on the received data, wherein a compliant push-up is a push-up meeting prescribed criteria; and monitor the number of compliant push-ups that have been performed.

The controller may be configured to use an algorithm to process the data received the at least one detection device, analyze the data, and re-establish the criteria for a compliant push-up. The remote device may include a user input device configured to receive input from a user of the remote device re-establishing the criteria for a compliant push-up. The remote device may include at least one of: a display configured to provide visual feedback when the respective user has performed a compliant push-up and/or configured to display the number of compliant push-ups that have been performed; and an audio output device configured to provide audible feedback when the respective user has performed a compliant push-up.

In some embodiments, the at least one detection device comprises a plurality of detection devices, each detection device including a unique identifier, and the controller of the remote device is configured to associate data received from a respective detection device with the respective detection device based on the unique identifier.

According to a fourth aspect, embodiments of the invention are directed to a method of detecting whether a compliant push-up has been performed. The method includes: establishing criteria for a compliant push-up; receiving data from an accelerometer of a detection device attached to or held by a user performing push-ups; and determining whether a compliant push-up has been performed based on the established criteria.

In some embodiments, the method includes: electronically collecting the data from the accelerometer; electronically analyzing the data; electronically automatically re-establishing the criteria for a compliant push-up. In some embodiments, the accelerometer is configured to trace a path of movement of the user, and the step of determining whether a compliant push-up has been performed includes determining a compliant push-up has been performed when the user has moved a threshold distance along the traced path of movement and/or a when the user has moved past a threshold position along the traced path of movement, wherein the threshold distance and/or the threshold position is based on the established criteria.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EMBODIMENTS OF THE INVENTION

Figure 1:
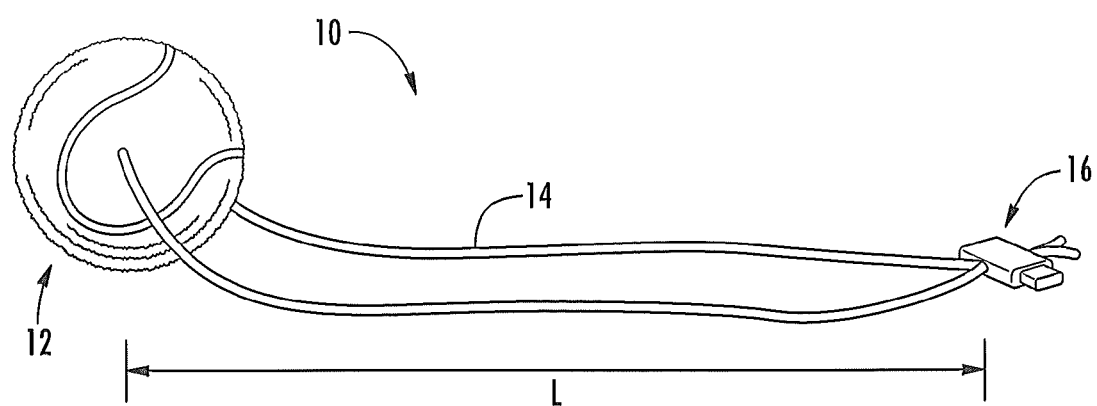
FIG. 1 is a schematic illustration of a portable exercise apparatus according to some embodiments.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the expression "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

As used herein, a "compliant push-up" is a push-up meeting prescribed criteria. The terms "correctly executed push-up" and "properly executed push-up" may also be used to refer to a compliant push-up. In some embodiments, a compliant push-up includes a push-up wherein, when the user is in the "down" position: the user's elbows are at 90 degrees, at generally 90 degrees or at substantially 90 degrees; the user's upper and lower arms define a right angle, generally define a right angle or substantially define a right angle; and/or the user's upper arms are parallel to, generally parallel to or substantially parallel to the ground.

FIG. 1 illustrates a portable exercise apparatus 10 according to some embodiments. The apparatus 10 includes a detection device 12. A suspension member 14 is adapted to suspend the detection device 12 away from the user. The suspension member 14 may be connected to and extend away from the detection device 12. In some embodiments, the suspension member 14 is flexible. As illustrated, the suspension member 14 is lanyard-like and includes two straps, strings or the like that extend away from the detection device 12 in a spaced-apart relationship and then converge to form a looped configuration. The suspension member 14 has a length L (i.e., each of the straps or strings has a length L) from the detection device 12 to an adjustment member, which is described below. In some embodiments, and as illustrated, the attachment member 14 is configured to loop around or hang/suspend from a user's neck, as described in more detail below. It is contemplated that the detection device 12 may be suspended from the user in different configurations.

An adjustment mechanism or member 16 is attached or connected to the suspension member 14. The adjustment member 16 is used to adjust the length L of the suspension member 14. The adjustment member 16 may be slidable relative to the suspension member 14. The adjustment member 16 may include a button, tab or the like that can be actuated to facilitate the sliding motion and/or lock the adjustment member 16 in place. Additionally or alternatively, the suspension member 14 may be friction-fit within the adjustment member 16.

Figure 2:
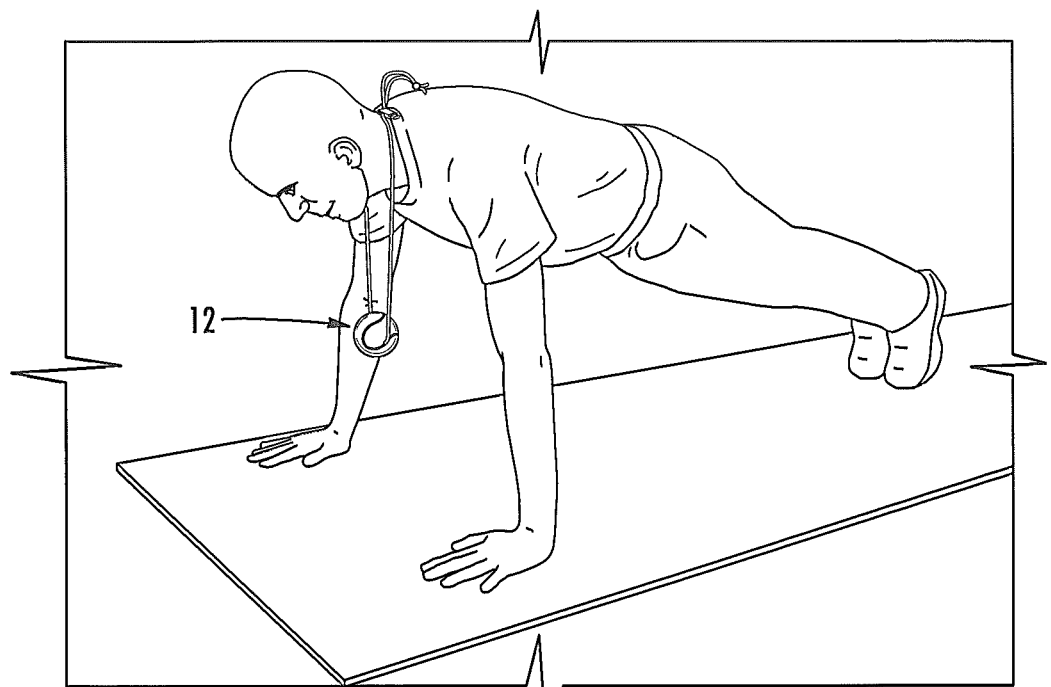
FIG. 2 is a schematic illustration of a user wearing the portable exercise apparatus of FIG. 1 in an "up" push-up position.
Figure 3:
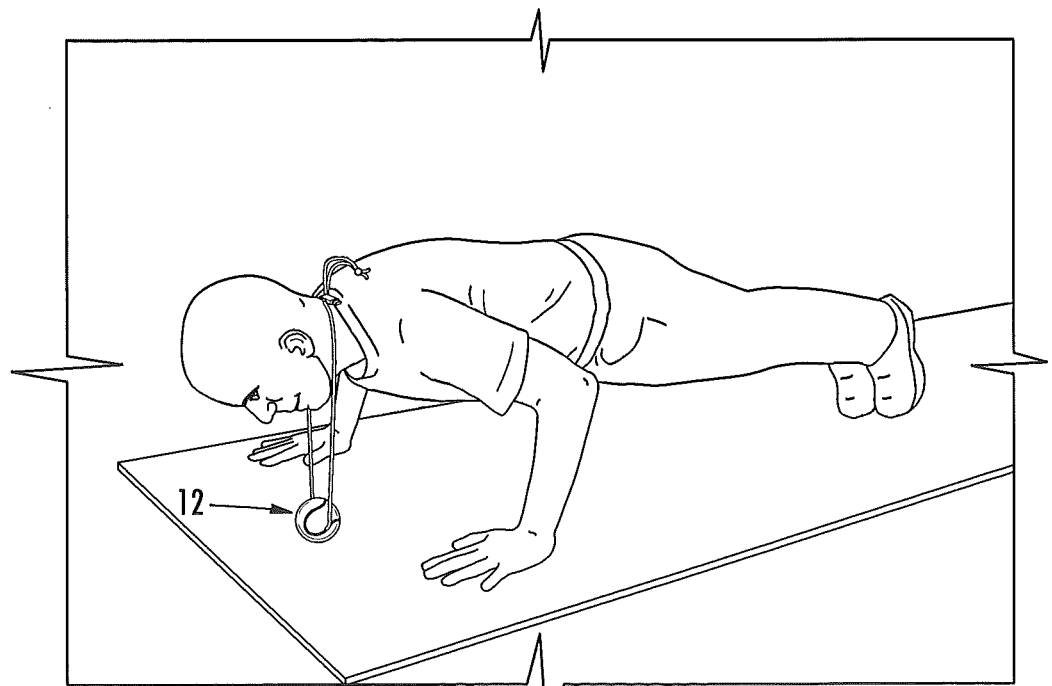
FIG. 3 is a schematic illustration of a user wearing the portable exercise apparatus of FIG. 1 in a "down" push-up position.

In use, the apparatus 10 is looped around the user's neck as shown in FIGS. 2 and 3, which illustrate a user performing a correctly executed push-up. The user moves between an "up" position (FIG. 2) and a "down" position (FIG. 3). In the up position, the user's upper arms are perpendicular to or generally perpendicular to the ground and the detection device 12 is suspended above the ground. In the down position, the user's upper arms are parallel to or generally parallel to the ground and the detection device 12 contacts the ground. FIG. 3 illustrates the 90 degree or right angle configuration of the user's elbow that defines a correctly executed push-up.

The adjustment member 16 allows the apparatus to be worn by users with varying body sizes (i.e., heights and, more specifically, forearm lengths). This is accomplished by adjusting the length L of the suspension member 14 to match or generally match the user's forearm length. In this regard, the suspension member 14 is adjusted such that the detection device 12 makes contact with the ground when the user's arm has formed a 90 degree angle thereby completing a correctly executed push-up.

Figure 4:
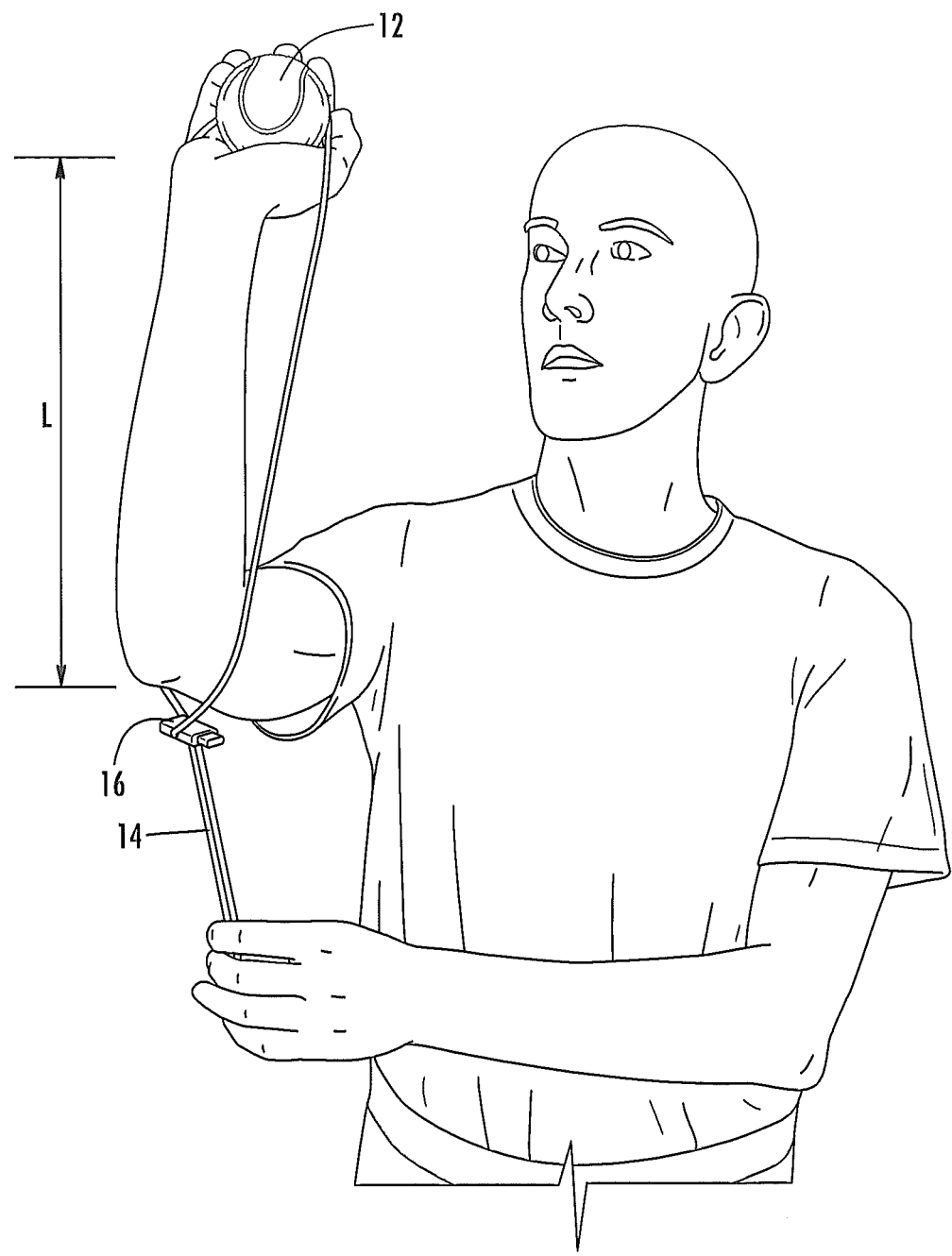
FIG. 4 is a schematic illustration of a user adjusting the portable exercise apparatus of FIG. 1.

This is exemplified in FIG. 4, wherein the adjustment member 16 and/or a portion of the suspension member 14 extending therethrough is manipulated with one hand while the detection device 12 is held in the other hand. The user may quickly and accurately adjust the apparatus to the correct length by adjusting the suspension member 14 and/or the adjustment member 16 snugly over the back of the elbow. This adjusts the length L of the suspension member 14 to roughly the length of the forearm, which is the correct distance so the detection device 12 reaches the ground when a correctly executed push-up has been performed. Thus, when adjusted correctly, the detection device 12 will touch the ground, thereby giving visual and/or proprioceptive feedback to the user that he/she is in the correct position (far down enough, and no need to go down further). This also allows the user to more accurately count the number of correctly performed push-ups in a set.

In some embodiments, the material and/or the geometry (e.g., width) of the suspension member 14 is selected to inhibit swaying of the detection device 12 during use. In addition, the material and/or the geometry of the suspension member 14 may be selected such that the apparatus is comfortable during use. The suspension member 14 may be made of a waterproof material so as to not absorb sweat produced during exercise. The material of suspension member 14 may be selected so as to be durable under a variety of conditions to inhibit ripping, tearing and other damage. In various embodiments the suspension member 14 may be made of a natural fiber and/or a synthetic material such as an elastomer or a polymer.

In the embodiments illustrated in FIGS. 1-4, the detection device 12 is a tennis ball. This provides a simple and inexpensive design that also provides audible, tactile, visual and/or proprioceptive feedback when the user has reached the proper "down" position. Other objects may be used for the detection device including other types of balls or other non-spherical objects. The shape and/or weight of the detection device may be selected to accommodate user comfort and minimize swaying during use.

Figure 5:
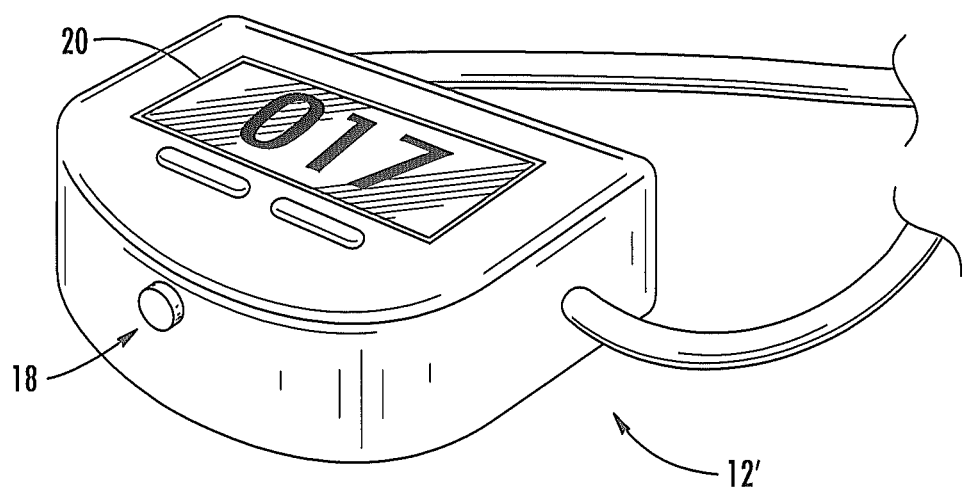
FIG. 5 is a schematic illustration of a portable exercise apparatus according to some other embodiments.

A detection device 12' according to some other embodiments is shown in FIG. 5. The detection device 12' includes a housing, body or case and is attached to a suspension member like the detection device 12. The detection device 12' may take the form of a counter and feedback device. In some embodiments, the detection device 12' comprises a mechanical, electro-mechanical or electrical counter including a button 18 (or other actuating device) and a display 20 that incrementally displays the number of times the button 18 has been depressed. The detection device 12' may be configured, positioned and sized such that the button 18 is depressed when the user has reached the proper "down" position. The user (or a monitor) may therefore read the display 20 to determine the number of correctly executed push-ups performed during and/or after completing a set. The button 18 and/or display 20 may also provide audible feedback such as a "click" to indicate to the user that he/she has reached the proper down position.

In some other embodiments, the detection device 12' includes a micro-switch and a counter in a manner similar to described above.

Figure 6:
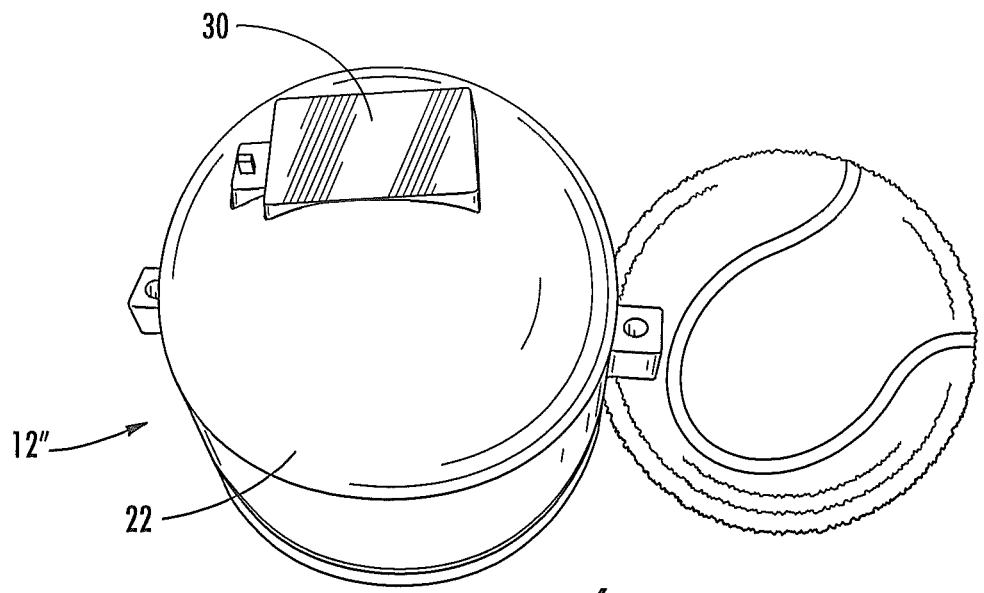
FIG. 6 is a schematic illustration of a detection device including a cover according to some embodiments of the invention.
Figure 7:
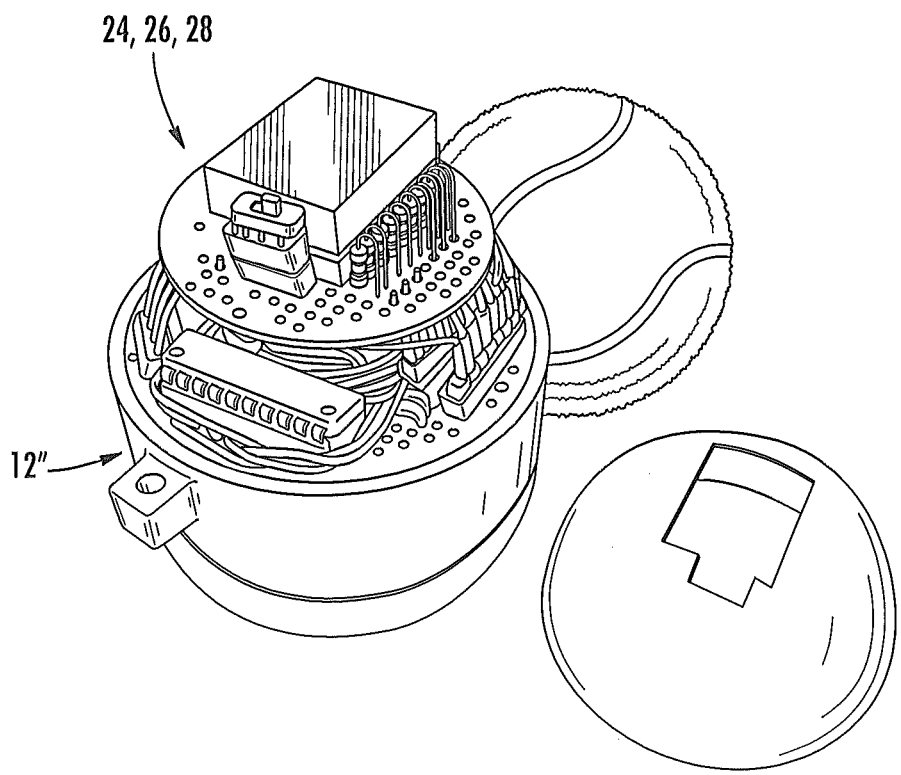
FIG. 7 is a schematic illustration of the detection device of FIG. 6 with the cover partially removed revealing components including an accelerometer.

A detection device 12" according to some other embodiments is shown in FIGS. 6 and 7. The detection device 12" includes a body, case, housing or outer shell 22 enclosing an electrical circuit 24. The housing 22 may be constructed of any suitable material (e.g., polymeric, metallic, etc.). The electrical circuit 24 includes at least one electrical sensor such as an accelerometer 26. The accelerometer 26 detects the full range of motion performed during each push-up. That is, the accelerometer 26 traces a path of movement between the "up" position and the "down" position while the user is performing push-ups.

The detection device 12" may include other components, such as a controller 28 and a display 30. The controller 28 may be used to receive and/or process signals from the accelerometer 26. For example, the controller 28 may be configured to analyze the path of movement of the accelerometer 26 to programmatically determine whether a push-up has been performed correctly and/or to cause a corresponding increment on the display 30. The term "programmatically" refers to operations directed and/or primarily carried out electronically by computer program modules, code and instructions.

Figure 8:
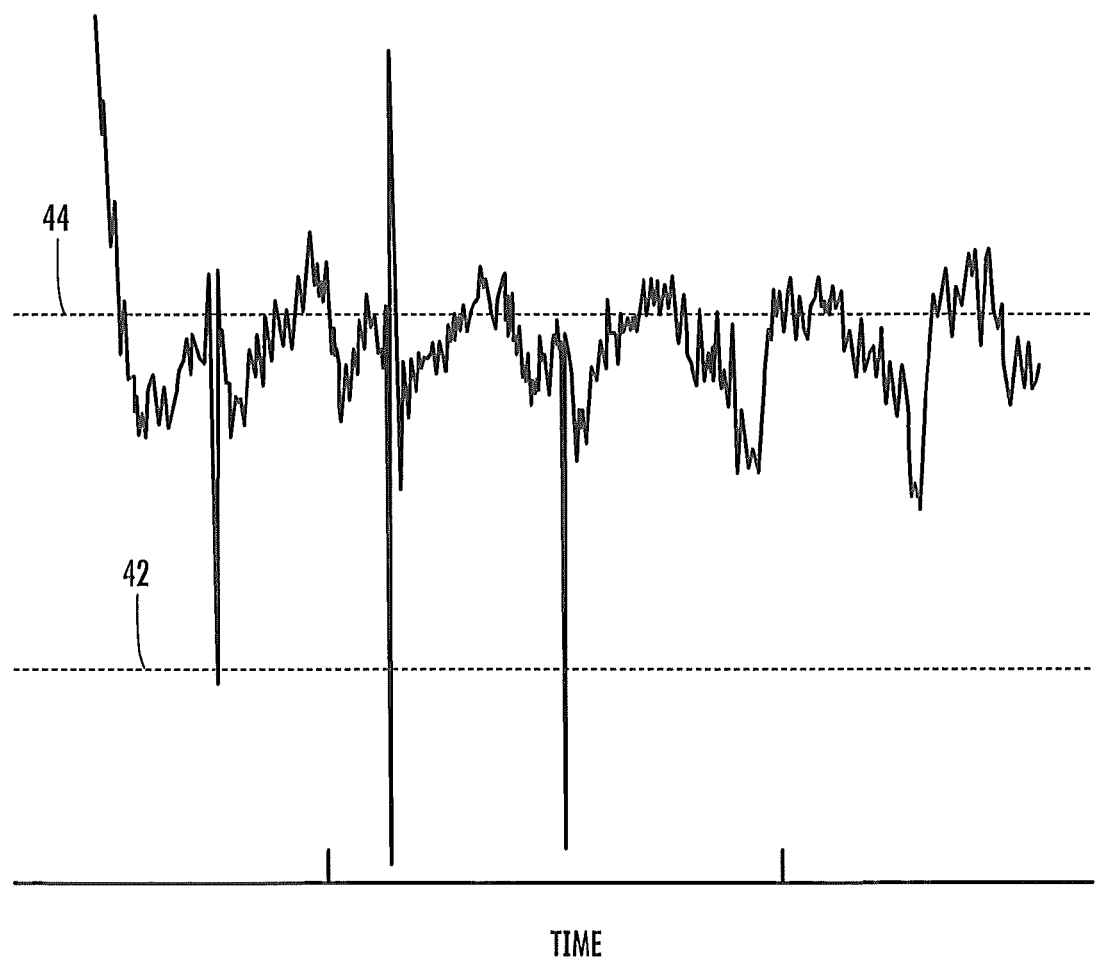
FIG. 8 is a graph illustrating an exemplary trace using the device and accelerometer of FIG. 7.

An exemplary accelerometer trace representing an output signal from the accelerometer 26 over time during use is shown in FIG. 8. The controller 28 or other component may analyze the data to determine whether a correctly executed push-up has been performed. For example, it may be determined that a user has reached the proper "down" position if the trace passes a predetermined threshold value (e.g., the threshold 42 in FIG. 8). Similarly, the trace may be analyzed to determine whether the user has passed a threshold value associated with the proper "up" position (e.g., the threshold 44 in FIG. 8). As can be seen in FIG. 8, the first three traces indicate that a correctly executed push-up has been performed while the last two traces indicate otherwise (i.e., that the user did not reach the proper 90 degree down position).

As described above, the controller 28 of the detection device 12" may be configured to receive data from the accelerometer 26 and determine whether a compliant push-up has been completed based on the received data. In some embodiments, the controller 28 may process the data received from the accelerometer 26 using one or more algorithms as described below.

In some embodiments, a sampling and post-processing algorithm is used to distinguish between correctly performed push-ups and incorrect push-ups or non push-up movement (for example, push-up not performed low enough for the detection device to contact the ground; multiple rapid vertical oscillations due to heavy contact of the detection device with the ground; abnormally frequent contacts due to incomplete "up" position during the push-up). Elements of the algorithm may include: (a) signal sampling frequency (Hz); (b) signal smoothing algorithm; (c) a time-censoring window (or "time delay" function); and (d) pattern-recognition algorithms.

According to some embodiments, the data are saved in memory for later analysis and/or processing. The algorithm may be corrected, for example, to account for a particular user's body type.

According to some embodiments, the user or other operator may establish the criteria for a compliant push-up (for example, different criteria may be established for users of different body types or different strengths). The criteria may be altered based on analysis of the data. The criteria may be changed manually by the user or operator or may be altered automatically by use of an algorithm.

Referring again to FIGS. 6 and 7, the controller 28 of the detection device 12" may count or track the number of push-ups that the user has correctly performed. Thus, the controller 28 may communicate with the display 30 to display an increase based on an analysis of the accelerometer signal and a determination that the push-up has been correctly performed. A two-digit counter display may be sufficient for most users, although a three-digit or more counter display is contemplated (for example, for use by military personnel).

It is contemplated that any of the detection devices described above may include an audio output device or transducer such that, when the detection device makes contact with the ground, audible feedback is provided to the user indicating completion of a correctly executed push-up. This may allow the user (or someone else judging, monitoring or observing), to easily determine that the push-up has been correctly executed and accurately count the number of correctly executed push-ups. It is noted that, with the accelerometer-based detection device, the detection device need not contact the ground when the user reaches the correct down position as the determination of whether the push-up was correctly performed may be determined based on a distance of the accelerometer travel. In these instances, an audible alert may be additionally useful to signal that the user has reached the proper 90 degree down position and/or has completed a correctly executed push-up. It is further noted that, with the accelerometer-based detection device, the device need not be suspended from the user. The device may be held by or on the user. For example, the device may be attached to the user using any suitable attachment mechanism, including straps, adhesive, clips, hook and loop fasteners and so forth. The device may also be held in a pocket or other compartment of the user's clothing. In some embodiments, the device is stably carried by or attached to the user so as to only or primarily detect up-and-down movement associated with push-ups.

Furthermore, the detection devices described above may wirelessly communicate (e.g., via Bluetooth or WIFI) with remote or outside devices that are remote from the detection device and, in some embodiments, remote from the user performing push-ups. For example, the detection device may include a transceiver or transmitter to transmit information to the remote device. This may be useful in a classroom setting, for example, where only one teacher is available to assess the performance of several students. Each detection device may communicate to the remote device various information such as whether a correctly executed push-up has been performed, the number of correctly executed push-ups that have been performed, the number of incorrectly executed push-ups that have been performed, the amount of time that has elapsed between the first and the last correctly executed push-up, and so on. Each detection device may include a unique electronic identifier such that the remote device can associate particular transmitted information with a particular detection device.

Figure 9:
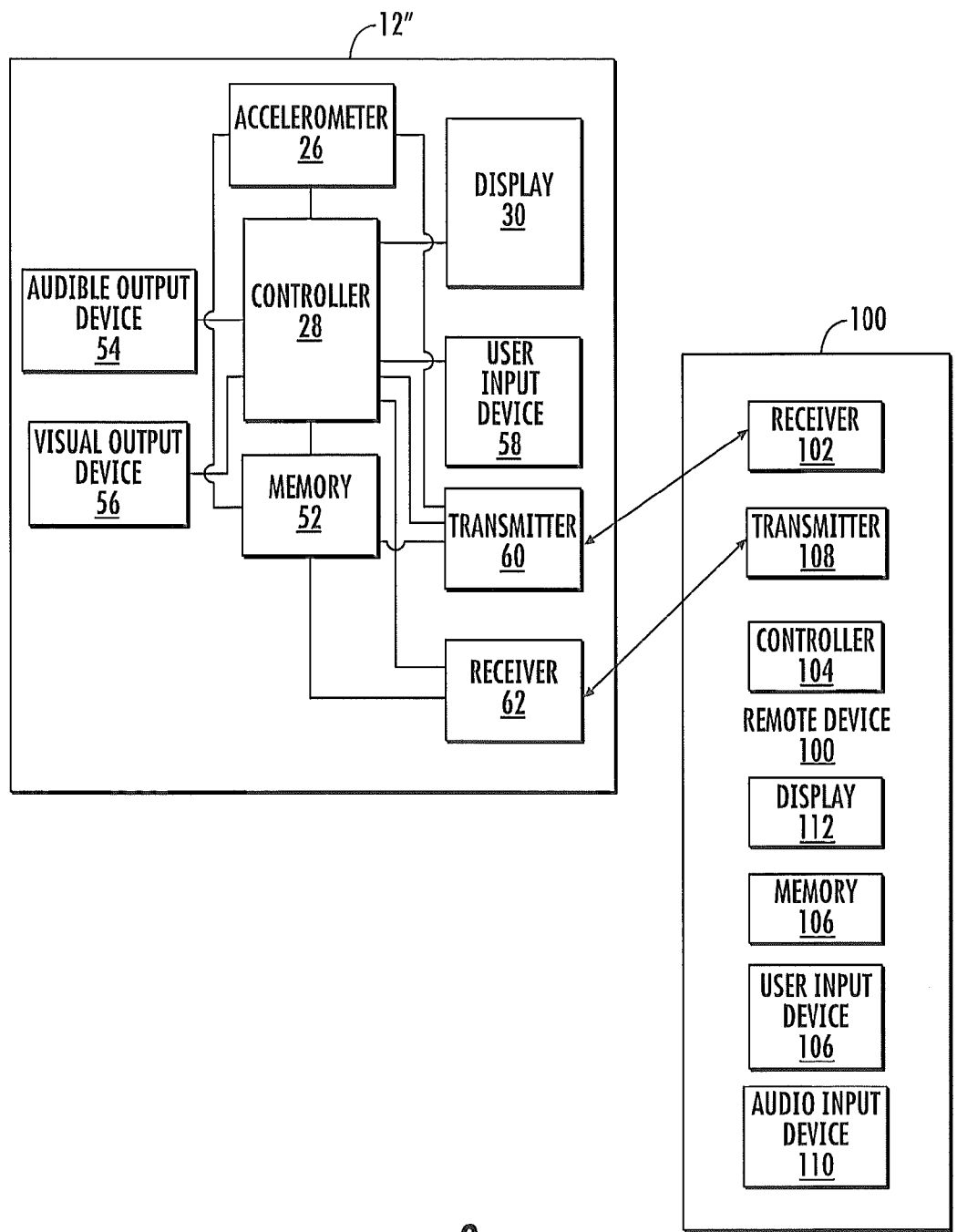
FIG. 9 is a block diagram illustrating the detection device of FIG. 6 and an optional remote device.

Referring to FIG. 9, the detection device 12" includes the accelerometer 26, the controller 28 and the display 30. In some embodiments, the display 30 may be omitted, for example if the device 12" is configured to communicate with an outside or remote device that includes a display, as will be described in greater detail below. The device 12" includes a power source 50 for supplying power to the device 12" and the components thereof. In some embodiments, the power source 50 is a battery. In some embodiments, the power source 50 is rechargeable, for example by connecting the device 12" to a power outlet or other power supply.

The device 12" may include memory 52. Data from the accelerometer 26 and/or the controller 28 may be saved in the memory 52 for later analysis and/or processing, including using algorithms as described above. The device 12" may include an audible output device 54 which may provide audible feedback when a user has performed a compliant push-up (or performed a non-compliant push-up). The display 30 or other visual output device 56 (e.g., an indicator light or LED) may provide visual feedback when a user has performed a compliant push-up (or performed a non-compliant push-up). The detection device 12" may include a user input device 58. The user input device 58 may be used to manually establish and/or alter criteria associated with a compliant push-up.

The detection device 12" may include a transmitter or transceiver 60 configured to wirelessly send signals including data from the accelerometer 26, the controller 28 and/or the memory 52 to one or more outside or remote devices 100. The remote device 100 illustrated in FIG. 9 includes a receiver 102 configured to wirelessly receive signals from the device 12". In some embodiments, the remote device may 100 receive the accelerometer data from accelerometer 26 of the detection device and a controller 104 of the remote device 100 may analyze and/or process the data to make determinations on whether push-ups are correctly performed. The controller 104 may be configured to automatically re-establish criteria for compliant push-ups based on the processing and/or analysis of the data. Thus, the controller 104 of the remote device 100 may perform the operations described above in connection with the controller 28 of the detection device 12".

Alternatively, a user of the remote device may use a user input device 106 to re-establish criteria associated with a particular device 12". For example, the user of the remote device 100 may observe the data received from the detection device 12" and determine that the criteria for a compliant push-up associated with that device 12" is too stringent or too lenient. Thus, the user of the remote device 100 may dynamically update or re-establish the criteria for a particular detection device 12", much like the controller 28 of the detection device 12" and/or the controller 104 of the remote device 100 may automatically do in the embodiments described above. The remote device 100 may include a transmitter or transceiver 108 to wirelessly transmit signals to a particular detection device 12" to re-establish the criteria for a compliant push-up at that device 12". The signals sent from the remote device transmitter 108 may be wirelessly received at a receiver 62 of the detection device 12" for re-establishment of the criteria. For example, the signals may be communicated to the controller 28 of the detection device 12" for re-establishment of the criteria.

The outside or remote device 100 may include an audio output device 110 which may provide audible feedback when a user has performed a compliant push-up (or performed a non-compliant push-up). The remote device 100 may include a display 112 or other visual output device (e.g., an indicator light or LED) to provide visual feedback when a user has performed a compliant push-up (or performed a non-compliant push-up) and/or display the number of determined compliant and/or non-compliant push-ups. The display 112 may be used by an operator of the remote device 100 to dynamically monitor a plurality of detection devices 12" at once.

The remote device 100 may include memory 114. Data (e.g., data from the accelerometer 26 of the device 12") may be saved in the memory 114 for later analysis and/or processing, including using algorithms as described above.

As noted above, a plurality of detection devices 12" may be employed, and each of the detection devices 12" may be in wireless communication with the outside or remote device 100. The remote device 100 may be able to distinguish between the plurality of detection devices (e.g., in the classroom). Each detection device 12" may include a unique identifier that is used to identify which data or signals are being sent from a particular detection device 12".

In various embodiments, the outside or remote device 100 may be a display, a personal computer, a tablet computer, a smartphone or any other type of device capable of receiving a wireless transmission.

EXAMPLE(S)

An apparatus similar to the one illustrated in FIGS. 1-4 has been tested. The purpose of the testing was to examine the usefulness of the apparatus to improve the reliability of teacher and student assessors in determining correct 90 degree push-ups. The methods were as follows: 1) Two fifth grade classes (N=40) were tested twice seven days apart; 2) Intervention group used the apparatus; 3) Control group did not use the apparatus; and 4) A student and teacher scored each performer on both trials.

The results shown in Table 1 were observed. It is noted that the reliability estimates were consistently higher when the apparatus was used.

TABLE 1

|  | With Apparatus | Without Apparatus |
|---|---|---|
| Interrater Rxx |  |  |
| Teachers | 0.95 | 0.88 |
| Students | 0.93 | 0.63 |
| Test-retest Rxx |  |  |
| Teachers | 0.89 | 0.88 |
| Students | 0.89 | 0.81 |

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:
1. A portable exercise apparatus for use by a user performing push-ups, the apparatus comprising:
 a detection device; and
 a suspension member connected to and extending away from the detection device in a looped configuration, the suspension member adapted to suspend the detection device froth the user's neck;

wherein, when the detection device is suspended from the user's neck by the suspension member, the apparatus is operative to indicate execution of a compliant push-up by the user;

wherein the suspension member has a length, the apparatus further comprising an adjustment member connected to the suspension member, the adjustment member configured to adjust the length of the suspension member;

wherein the length of the suspension member is adjustable to a user's forearm length by receiving the detection device in the user's palm with the user's elbow at a substantially right angle, looping the attachment member beneath the user's elbow and moving the adjustment member upward until it resides against or proximate the user's elbow;

wherein the user performs push-ups between an up position and a down position, and wherein, when the length of the suspension member is adjusted to the user's forearm length:

in the up position, the user's upper arm is substantially perpendicular to the ground and the detection device is suspended above the ground; and in the down position, the user's upper arm is substantially parallel to the ground and the detection device contacts the ground.

2. The apparatus of claim 1, wherein, in the down position, the detection device provides audible, tactile, visual and/or proprioceptive feedback.

3. The apparatus of claim 1, further comprising an actuator disposed on the detection device, wherein in the down position, the detection device contacts the ground such that the actuator is actuated.

4. The apparatus of claim 3, further comprising a counter disposed on the detection device, the counter configured to incrementally display a number of times the actuator is actuated.

5. A portable exercise apparatus for use by a user performing push-ups, the apparatus comprising:

a detection device attached to or carried by the user, the detection device comprising:
a housing;
an accelerometer held in the housing, wherein the accelerometer is configured to trace a path of movement of the user; and
a controller held in the housing, the controller configured to:
receive data from the accelerometer;
determine when a compliant push-up has been performed based on the received data including when the user has moved a threshold distance along the traced path of movement and/or a when the user has moved past a threshold position along the traced path of movement, wherein a compliant push-up is a push-up meeting prescribed criteria;
electronically process the data received from the accelerometer, analyze the data, and re-establish the criteria for a compliant push-up based On the analysis of the data; and
monitor the number of compliant push-ups that have been performed.

6. The apparatus of claim 5, wherein the threshold distance and/or the threshold position is based on the prescribed criteria.

7. The apparatus of claim 5, wherein the detection device includes at least one of:

a display configured to display the number of compliant push-ups that have been performed; and
an audio output device configured to provide audible feedback when the user has performed a compliant push-up.

8. A system for monitoring push-ups, the system comprising:

at least one detection device, each one attached to or carried by a respective user, each detection device comprising:
a housing;
an accelerometer held in the housing, wherein the accelerometer is configured to trace a path of movement of the user; and
a transmitter configured to wirelessly transmit data from the accelerometer; and
a remote device comprising:
a receiver configured to wirelessly receive data transmitted from the at least one detection device; and
a controller configured to:
determine when a compliant push-up has been performed based on the received data including when the user has moved a threshold distance along the traced path of movement and/or a when the user has moved past a threshold position along the traced path of movement, wherein a compliant push-up is a push-up meeting prescribed criteria;
electronically process the data received from the at least one detection device, analyze the data, and re-establish the criteria for a compliant push-up; and
monitor the number of compliant push-ups that have been performed;
wherein the remote device further comprises a user input device configured to receive input from a user of the remote device re-establishing the criteria for a compliant push-up.

9. The system of claim 8, wherein the remote device includes at least one of:

a display configured to provide visual feedback when the respective user has performed a compliant push-up and/or configured to display the number of compliant push-ups that have been performed; and
an audio output device configured to provide audible feedback when the respective user has performed a compliant push-up.

10. The system of claim 8, wherein the at least one detection device comprises a plurality of detection devices, each detection device including a unique identifier, and wherein the controller of the remote device is configured to associate data received from a respective detection device with the respective detection device based on the unique identifier.

11. A method of detecting whether a compliant push-up has been performed, the method comprising:

establishing criteria for a compliant push-up;
receiving data from an accelerometer of a detection device attached to or held by a user performing push-ups, wherein the accelerometer is configured to trace a path of movement of the user;
electronically collecting the data from the accelerometer;
determining whether a compliant push-up has been performed based on the established criteria, wherein determining whether a compliant push-up has been performed comprises determining a compliant push-up has been performed when the user has moved a threshold distance along the traced path of movement and/or a when the user has moved past a threshold position along the traced path of movement, wherein the threshold distance and/or the threshold position is based on the established criteria;

electronically analyzing the data collected from the accelerometer; and electronically automatically re-establishing the criteria for a compliant push-up based on the analyzed data.

12. The apparatus of claim 1, wherein the adjustment member comprises a locking mechanism for locking the adjustment member in place.

13. The apparatus of claim 1, wherein the suspension member is friction-fit within the adjustment member.

14. The apparatus of claim 1, wherein the detection device is a ball.

* * * * *

UNITED STATES PATENT AND TRADEMARK OFFICE
CERTIFICATE OF CORRECTION

PATENT NO. : 9,452,318 B2  
APPLICATION NO. : 13/833062  
DATED : September 27, 2016  
INVENTOR(S) : Rowe et al.

Page 1 of 1

It is certified that error appears in the above-identified patent and that said Letters Patent is hereby corrected as shown below:

In the Claims

Column 11, Claim 5, Line 59: Please correct "based On the"
to read -- based on the --

Signed and Sealed this
Twenty-fifth Day of April, 2017

Michelle K. Lee
*Director of the United States Patent and Trademark Office*